(12) United States Patent
Oslund et al.

(10) Patent No.: US 6,793,648 B2
(45) Date of Patent: Sep. 21, 2004

(54) BACK-LOADING CATHETER

(75) Inventors: John C. Oslund, Cottage Grove, MN (US); Richard S. Kusleika, Eden Prairie, MN (US); Kent D. Anderson, Champlin, MN (US); Cheryl A. Videen, Stacy, MN (US)

(73) Assignee: ev3 Inc., Plymouth, MN (US)

( * ) Notice: Subject to any disclaimer, the term of this patent is extended or adjusted under 35 U.S.C. 154(b) by 0 days.

(21) Appl. No.: 10/369,406

(22) Filed: Feb. 14, 2003

(65) Prior Publication Data

US 2003/0125667 A1 Jul. 3, 2003

Related U.S. Application Data

(63) Continuation of application No. 09/631,482, filed on Aug. 3, 2000, now Pat. No. 6,527,746.

(51) Int. Cl.[7] ............................................. A61M 5/178
(52) U.S. Cl. ...................................... 604/160; 604/264
(58) Field of Search ................................. 604/160, 158, 604/264; 606/200

(56) References Cited

U.S. PATENT DOCUMENTS

| | | |
|---|---|---|
| 4,054,136 A | 10/1977 | Von Zeppelin |
| 4,585,013 A | 4/1986 | Harris |
| 4,988,356 A | 1/1991 | Crittenden et al. |
| 5,135,535 A | 8/1992 | Kramer |
| 5,163,911 A | 11/1992 | Sirimanne et al. |
| 5,171,222 A * | 12/1992 | Euteneuer et al. .......... 604/102 |
| 5,195,978 A | 3/1993 | Schiffer |
| 5,234,407 A | 8/1993 | Teirstein et al. |
| 5,263,932 A | 11/1993 | Jang |
| 5,281,203 A | 1/1994 | Ressemann |
| 5,324,269 A | 6/1994 | Miraki |
| 5,334,187 A | 8/1994 | Fischell et al. |
| 5,380,290 A | 1/1995 | Makower et al. |
| 5,409,469 A | 4/1995 | Schaerf |
| 5,489,271 A | 2/1996 | Andersen |
| 5,709,658 A * | 1/1998 | Sirhan et al. ............... 604/102 |
| 5,795,322 A | 8/1998 | Boudewijn |
| 5,807,355 A | 9/1998 | Ramzipoor et al. |
| 5,814,064 A | 9/1998 | Daniel et al. |
| 5,848,964 A | 12/1998 | Samuels |
| 5,891,056 A | 4/1999 | Ramzipoor |
| 5,919,164 A | 7/1999 | Andersen |
| 5,941,896 A | 8/1999 | Kerr |
| 5,947,995 A | 9/1999 | Samuels |
| 6,001,118 A | 12/1999 | Daniel et al. |
| 6,010,522 A | 1/2000 | Barbut et al. |
| 6,053,932 A | 4/2000 | Daniel et al. |
| 6,056,720 A | 5/2000 | Morse |
| 6,074,357 A | 6/2000 | Kaganov et al. |
| 6,110,146 A | 8/2000 | Berthiaume et al. |
| RE36,857 E * | 9/2000 | Euteneuer et al. .......... 604/102 |
| 6,168,579 B1 | 1/2001 | Tsugita |
| 6,206,852 B1 | 3/2001 | Lee |
| 6,245,089 B1 | 6/2001 | Daniel et al. |
| 6,248,092 B1 | 6/2001 | Miraki et al. |
| 6,450,987 B1 | 9/2002 | Kramer |
| 6,537,295 B2 | 3/2003 | Petersen |
| 6,616,681 B2 | 9/2003 | Hanson et al. |
| 2002/0042626 A1 | 4/2002 | Hanson et al. |
| 2003/0045372 A1 | 1/2003 | Boyle et al. |
| 2003/0153942 A1 | 8/2003 | Wang et al. |
| 2003/0176887 A1 | 9/2003 | Petersen |
| 2004/0019363 A1 * | 1/2004 | Hanson et al. .............. 606/200 |

FOREIGN PATENT DOCUMENTS

| | | |
|---|---|---|
| EP | 0 737 450 A1 | 10/1996 |
| WO | WO 03/002035 A2 | 1/2003 |

* cited by examiner

Primary Examiner—Marc Norman
(74) Attorney, Agent, or Firm—Popovich, Wiles & O'Connell, P.A.

(57) ABSTRACT

A catheter provided with a collapsible inner lumen within a main body. The catheter can deploy a distal protection device using a guidewire which is threaded through the inner lumen, the inner lumen collapsing upon retrieval of the device into the catheter main body.

26 Claims, 2 Drawing Sheets

BACK-LOADING CATHETER

This is a continuation of application Ser. No. 09/631,482 filed on Aug. 3, 2000 now U.S. Pat. No. 6,527,746.

FIELD OF THE INVENTION

The present invention relates to medical treatment apparatus, such as distal protection devices, deployed in a vessel of the body. In one of its more particular aspects this invention relates to the retrieval of such devices. More specifically, the invention relates to a catheter designed for ready retrieval of medical devices.

BACKGROUND OF THE INVENTION

Any intervention into the human vasculature that uses a guidewire or medical device attached to a guidewire may require back-loading the catheter during the course of the medical procedure. Back loading a guidewire into a catheter from the distal end of the catheter to an exit port positioned proximal from the distal end of the catheter can be difficult without a guiding means. To facilitate back-loading, a guidewire lumen, separate from the catheter main body, may be used. Such a separate lumen can run from proximate the distal end of the catheter to a desired exit location proximate the guidewire entry location.

Medical apparatus, such as distal protection devices, are utilized in both over-the-wire and rapid exchange type catheters. While, typically, there are no unique problems encountered during deployment of such devices, problems can be encountered during device retrieval after an interventional procedure.

During the course of a medical procedure, the need may arise to capture debris, such as grumous matter, emboli, thrombi from the affected vessel. Filters of various types have found use, for example, in trapping blood clots and other debris released into the blood stream. Filters are traps that have been designed to be used to collect dislodged matter such as described above. They serve to provide protection from distal embolization that might result in a major adverse coronary event or other acute complication. Embolization of debris which might be released during such procedures and the resulting sequellae have been described in reports documenting major adverse cardiac event rates. Such events include acute myocardial infarction, revascularization and even death.

In order to address such acute embolic-related complications, distal filtration and protection devices have been developed. Such devices have been designed to work with existing interventional modalities. Such devices provide debris-filtering protection during invasive procedures and are intended to prevent complications of particulate embolization.

Such distal filtration and protection devices are typically deployed at a location along a vessel of the body at a desired location. Such deployment is performed by extending the device outwardly from the distal end of a catheter. In order to facilitate deployment, the device to be deployed typically has components made from a shape-memory or highly elastic material. Consequently, they are able to be collapsed within the catheter and, upon being urged outwardly beyond the distal end of the catheter, they reassume their uncollapsed shape.

Once in place, the protection device performs the function of filtering debris as discussed above. Retrieval of a debris-filled filter offers unique problems.

Since the retrieval of a distal protection device requires a minimum inside diameter to remove the device filled with captured debris, it can be difficult to retrieve a device into a recovery catheter. In order to facilitate back-loading, a separate guidewire lumen may be used. Such a lumen must be configured, however, to be retracted within the catheter main body to afford access to the distal protection device during retrieval. If the lumen does not move, or allow retrieval of the distal protection device into the catheter main body, the captured debris will not be properly retrieved into the distal end of the recovery catheter.

Alternatively, debris may be removed from the distal protection device by means of suction while the distal protection device is still deployed in the vasculature. Suction through the catheter main body could aspirate captured debris from the distal protection device using a syringe or similar device attached to the proximal end of the catheter. Since the main body could be sealed off from the guidewire lumen, pressure losses would not occur resulting in decreased aspiration performance.

No device has yet been developed which is effective to accomplish debris removal in a simple manner.

SUMMARY OF THE INVENTION

It is an object of the present invention to provide a catheter in which the removal of debris can be accomplished in a simple, effective manner.

Another object of the invention is to facilitate retrieval of a distal protection device or other medical apparatus.

Another object of the invention is to simplify back-loading a guidewire and device carried by the guidewire into a large inside diameter catheter.

Another object of this invention is to facilitate effective aspiration from a filter deployed in a body vessel.

Other objects and advantages of the present invention will become apparent from the following DETAILED DESCRIPTION OF THE INVENTION.

The catheter of the present invention, in one embodiment, is provided with a collapsible inner lumen which can be used to back-load a guidewire or a device having been deployed on a guidewire. The catheter comprises a catheter main body which is equipped, in that embodiment, with a collapsible inner lumen. The inner lumen is adapted to receive the guidewire. The guidewire may be fed, external of the patient being treated, into the lumen through the distal end of the lumen. The guidewire was previously inserted into the patient mounting a medical device such as a distal protection device. Following its use to capture debris, the protection device is retrieved. Upon retrieval the inner lumen collapses, allowing the filter basket containing debris to be received into the catheter main body.

The collapsible inner lumen can serve as a guidewire conduit extending from the distal end of the catheter main body to a proximal location at the exit port.

It may be appropriate to aspirate through the catheter to remove debris from the filter basket prior to retrieval. Having the inner lumen of the present invention communicating with, and sealed at, the exit port, the present catheter has been found to be an effective way of preventing pressure losses during aspiration, since the lumen is isolated from the interior of the main body of the catheter.

The inner lumen of this embodiment of the catheter of the present invention can be constructed from a variety of thin-walled flexible tubing materials such as thin-walled polytetrafluoroethylene tubing. The thin-walled tubing-to be used as the inner lumen of the present invention should collapse when subjected to a minimal axial force, yet should have sufficient axial strength to prevent kinking during back-loading a guidewire. The minimal axial force for collapsing the inner lumen has been found to fall in the range of about 100 grams to about 500 grams.

The inner lumen can be recessed within the distal end of the catheter main body for about 15–40 cm in the proximal direction in a rapid exchange version. The inner lumen, in this embodiment, is fixed at a proximal end, and can be free floating or attached at the distal end, as desired.

In operation, a distal protection device such as a filter basket is pulled into the distal end of the catheter main body, and the inner lumen collapses under minimal force for retrieval.

In another embodiment of the present invention, the inner lumen is also fixed at a proximal end. As in the first embodiment discussed above, it can be free-floating or attached at its distal end. In this embodiment, however, the lumen does not collapse when subjected to a minimal axial force. Rather, a wall of the lumen is provided with a series of axially extending perforations. When the guidewire is withdrawn to retract, for example, a filter basket, the guidewire "cuts" the inner lumen axially along the line of perforation. The guidewire rides up the slit thereby formed, and the filter basket is retracted into the catheter main body passing alongside the inner lumen external with respect thereto.

A further embodiment of the invention includes an inner lumen which is not fixed at its proximal end with respect to the catheter main body. Rather, in this embodiment, the inner lumen is retractable through the exit port, in effect, to withdraw the distal end thereof to recess it within the catheter main body. Such retraction can be accomplished by retracting the guidewire external to the patient being treated.

The present invention is thus an improved catheter for back-loading a device such as a filter having previously been deployed on a guidewire in vasculature of an individual. More specific features and advantages obtained in view of those features will become apparent with reference to the DETAILED DESCRIPTION OF THE INVENTION, appended claims, and accompanying drawing figures.

DETAILED DESCRIPTION OF THE INVENTION

Figure 1:
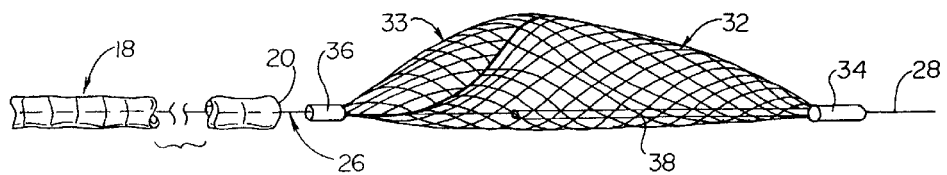
FIG. 1 is a fragmentary perspective view of an inner lumen as used in combination with a distal protection device in accordance with the present invention.

Referring now to the drawing figures wherein like reference numerals denote like elements throughout the several views, FIG. 1 illustrates a filter basket 32, of a type known in the prior art, having a defined open mouth 33 into which grumous material and the like can be caught during the performance of a medical procedure in vasculature of a patient. It will be understood that, while the invention is described herein with respect to positioning of a distal protection device in the vascular of an individual patient, the invention's scope extends beyond this specific application.

FIG. 1 illustrates filter basket 32 attached to a guidewire 26 by means of connection means. That figure illustrates a distal connector 34 which, typically, would be affixed at a defined axial point along guidewire 26. In most applications, this point of affixation would be proximate the distal end 28 of guidewire 26. FIG. 1 also illustrates guidewire 26 passing through a tube 38 carried by filter basket 32.

At the proximal or open end of filter basket 32, it is secured to guidewire 26 by proximal connector 36. While connector 36 can be rigidly connected to guidewire 26 at a defined axial location, it will be understood that, in some applications, it can be allowed to float along guidewire 26.

Guidewire 26, it will be understood, passes into the vasculature of the patient through a location of access. When it is appropriate to remove filter basket 32 from the anatomy of the patient, it would, typically, be filled with grumous material, emboli and/or other anatomical debris. It is, of course, desirable, and even essential, that such debris not be allowed to be redeposited within the vasculature. Various procedures have been used over the years to ensure compliance with these necessities.

The present invention is an improved catheter which can be used for back-loading a device such as a filter basket 32 into a recovery catheter to withdraw the distal protection device from the patient's vasculature. In order to facilitate this effort, the distal end 20 of an inner lumen 18 is fed over the guidewire at the point of access on the patient. While not essential, the distal end 20 of the inner lumen 18 can extend at least a short distance outwardly from a distal end 14 of a catheter main body 12. By so constructing the catheter in accordance with the present invention, guidewire 26 can be more easily fed into inner lumen 18.

Figure 2:
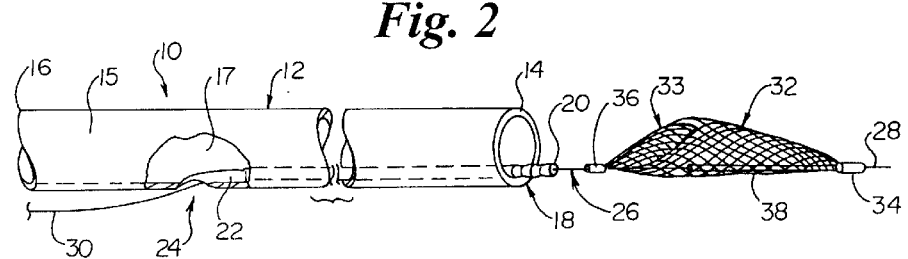
FIG. 2 is a detailed perspective view of the inner lumen/distal protection device of FIG. 1 as employed in a first embodiment of the invention prior to recovery of the distal protection device.

FIG. 2 illustrates a catheter main body 12 fed into the vasculature to a point where a distal end 20 of lumen 18 is closely proximate filter basket 32 and proximal connector 36 therefor. With the catheter main body 12 at this location, the individual performing the procedure can then withdraw guidewire 26, by grasping and drawing guidewire 26 at its proximal end 30, and retracting filter basket 32 into large inside diameter catheter main body 12.

FIG. 2 illustrates proximal end 22 of inner lumen 18 fixedly connected to wall 15 defining catheter main body 12 at exit port 24 and in communication with the outside of catheter main body 12 through port 24. It is in this manner that guidewire 26 is accessible to the surgeon or other person performing the procedure.

As will be able to be seen, however, distal end 20 of lumen 18, while having served an important function in positioning recovery catheter 10 for retraction of filter basket 32 into catheter main body 12, can to one degree or another obstruct retrieval of filter basket 32. The present invention, therefore, contemplates, in the embodiment of FIGS. 2 and 3, a lumen 18 wherein at least a portion of lumen 18 at the distal end 20 thereof is corrugated or accordion-like in construction. Inner lumen 18 can be made from a variety of thin-walled, flexible tubing materials. One particularly appropriate material is polytetrafluoroethylene. Such a material enables distal end 20 of lumen 18 to collapse when subjected to a minimal axial force such as that brought to bear upon it by filter basket 32. It is envisioned that distal end 20 of lumen 18 should be sufficiently strong so as to prevent kinking, but sufficiently weak so as to collapse when an axial force of between 100 grams and 500 grams is brought to bear.

Figure 3:
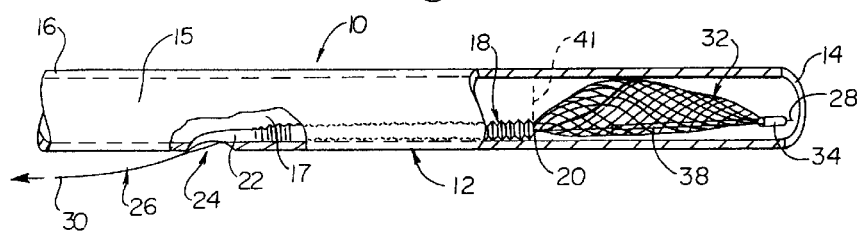
FIG. 3 is a perspective view of the embodiment of FIG. 1 in a recovered position.

While the embodiment illustrated in FIGS. 2 and 3 and described to this point specifically employs corrugations or accordion-like folds, it will be understood that this embodiment need not specifically employ such structure. In a preferred embodiment of the invention, the inner lumen 18 can merely be formed of a material that satisfies the desirable dictates for the invention but does not specifically have corrugations or accordion-like folds. That is, the wall defining lumen 18 can merely be sufficiently weak so as to collapse when subjected to the axial force brought to bear upon it by filter basket 32.

As seen in FIG. 3, a sufficient axial dimension of lumen 18 is provided with corrugation or accordion-like structure so that filter basket 32 can be housed within catheter main body 12 and be substantially fully retracted in a proximal direction wherein distal end 28 of guidewire 26 is in a proximal direction from distal end 14 of main body 12. With filter basket 32 in this position, aspiration by suction can be applied to catheter main body to remove the debris from basket 32. In order to facilitate such aspiration proximal end 22 of lumen 18 can be sealed and thereby isolated from channel 17 within main body 12 at exit port 24.

In this embodiment of the invention, the distal end 20 of lumen 18 defines a wall which is circumferentially continuous throughout a full 360°. Initially, that axial position is proximate distal end 14 of main body 12. As previously discussed, that location can be either slightly proximal or distal with respect to distal end 14 of main body 12. After lumen 18 collapses, however, that point becomes recessed within catheter main body 12 to a location illustrated at 41. Thus, filter basket 32 is able to be fully housed within catheter main body 12.

Figure 4:
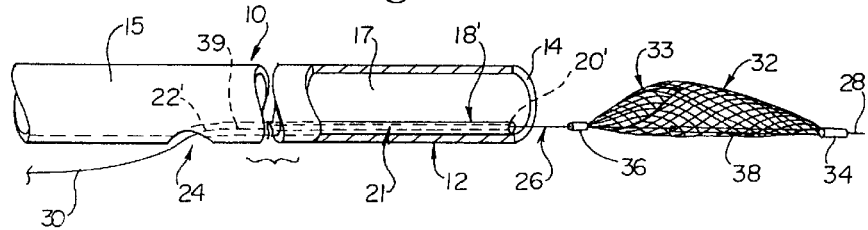
FIG. 4 is a detailed perspective view of the inner lumen/distal protection device of FIG. 1 as employed in a second embodiment of the invention prior to recovery of the distal protection device.
Figure 5:
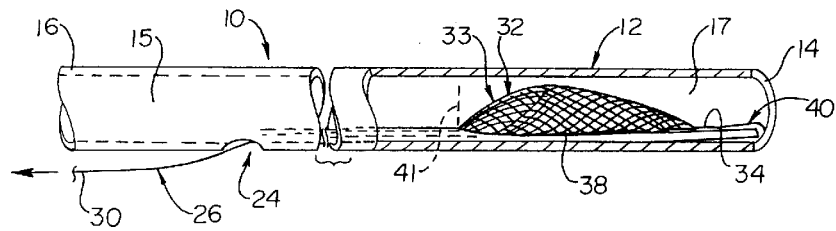
FIG. 5 is a perspective view of the embodiment of FIG. 4 in a recovered position.

Referring to FIGS. 4 and 5, a second embodiment of the invention is illustrated. The embodiment of FIGS. 4 and 5 is quite similar to that of FIGS. 2 and 3. In this embodiment, however, inner lumen 18' does not collapse. Still anchored and sealed at exit port 24 at its proximal end 22', lumen 18' does, nevertheless, allow for an apparent axial movement of the axial point at which lumen 18' is circumferentially continuous through a full 360°. This is accomplished by defining an axially extending line of perforation 21 in distal end 20' of lumen 18'. As guidewire 26 is retracted to draw filter basket 32 into main body 12 of catheter 10, engagement of fastener 36 with distal end 20' of lumen 18' will cause perforation line 21 to fracture and progressively define slot 40. As continued pressure is applied to draw filter basket 32 into channel 17 within main body 12, proximal fastener 36, attached to proximal end of filter basket 32, will ride externally along distal end 20' of lumen 18' as slot 40 is progressively opened. Filter basket 32 will then move inward within channel 17 in a proximal direction with respect to distal end 20' of lumen 18' until it achieves position 41, the adjusted location at which lumen 18' is circumferentially continuous through a full 360°. With filter basket 32 at this position, it will be fully housed within catheter main body 12.

Figure 6:
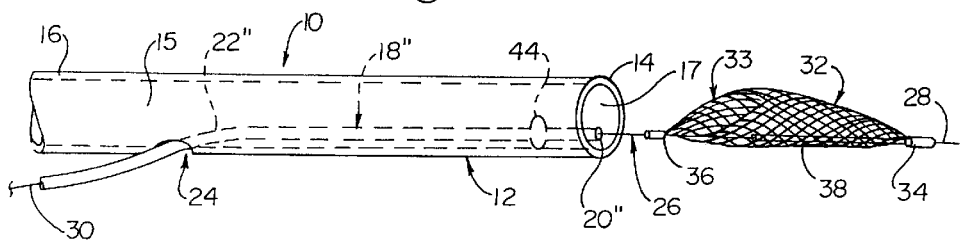
FIG. 6 is a detailed perspective view of the inner lumen/distal protection device of FIG. 1 as employed in a third embodiment of the invention prior to recovery of the distal protection device.
Figure 7:
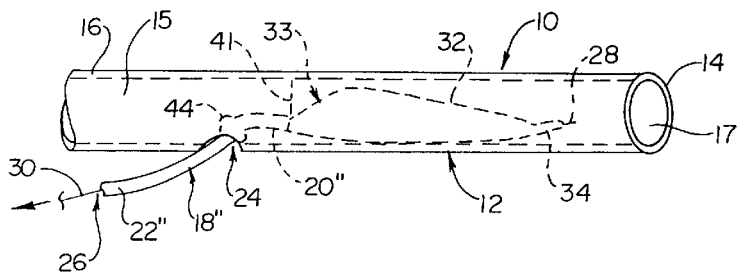
FIG. 7 is a perspective view of the embodiment of FIG. 6 in a recovered position.

FIGS. 6 and 7 illustrate a third embodiment in accordance with the present invention. In this embodiment, lumen 18" is not fixed at exit port 24. Rather, proximal end 22" of lumen 18" extends through, and is slidable with respect to, port 24. As in the case of the first two embodiments, distal end 20" of lumen 18" is initially located axially proximate distal end 14 of main body 12. Upon engagement of proximal connector 36 with distal end 20" of lumen 18", lumen 18" can be manually retracted through exit port 24. This will enable filter basket 32 to be fully housed within channel 17 in main body 12, as illustrated in FIG. 7. Again, while the circumferentially continuous through 360° location of the wall of lumen 18" was initially proximate distal end 14 of main body 12, FIG. 7 illustrates that axial point now being recessed within main body 12 to axial location 41.

While not essential to the invention, inner lumen 18", in this embodiment, can be provided with a stop 44 for limiting the distance to which filter basket 32 can be retracted. Stop 44 can comprise an annular bead formed about the outer wall of lumen 18". Positioning of stop 44 is, of course, at a location with respect to distal end 20" of lumen 18" so that full housing of filter basket 32 will be permitted.

Lumen 18" can, if desired, also be provided with a second stop (not shown). Such a second stop can be provided at an axial location along lumen 18" so that it is external to exit port,24. Such a stop would limit the ability to insert lumen 18" beyond a desired position within catheter main body 12.

In the case of all embodiments described, sealing of lumen 18, 18', 18" at exit port 24 can be provide in order to enable aspiration of debris from filter basket 32 as previously discussed. In the two embodiments of FIGS. 2–5, such sealing and isolation of the lumen at exit port 24 is accomplished by integrally molding proximal end 22, 22' at exit port 24. In the embodiment of FIGS. 6–7, such seal can take the form of any appropriate mechanical seal at exit port 24.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A catheter for recovering a medical device carried by a guidewire from a vessel or other tubular conduit in a human body comprising:

a tubular main body portion having distal and proximal ends and defining a first lumen sized to receive the medical device; and a guidewire receiving portion having distal and proximal ends and defining a second lumen sized for receiving the guidewire, the guidewire receiving portion being at least partially contained within the first lumen, the distal end of the guidewire receiving portion being moveable with respect to the main body portion from a first position before recovery of the medical device into the first lumen to a second position after recovery of the medical device into the first lumen, the distal end of the guidewire receiving portion extending distally of the distal end of the main body portion when the guidewire receiving portion is in the first position and the distal end of the guidewire receiving portion being contained with the first lumen proximal of the distal end of the main body portion when the guidewire receiving portion is in the second position.

2. The catheter according to claim 1, further comprising an exit port between the distal and proximal ends of the tubular main body.

3. The catheter according to claim 1, wherein the guidewire receiving portion includes a line of perforation begining at the distal end of the guidewire receiving portion.

4. The catheter according to claim 3, wherein during retraction of the guidewire receiving portion the line of perforation progressively opens.

5. The catheter according to claim 1, wherein the proximal end of the guidewire receiving portion extends through the exit port.

6. The catheter according to claim 1, wherein the guidewire receiving portion communicates external to the catheter through the exit port.

7. The catheter according to claim 1, wherein the medical device is a filter basket.

8. A catheter for recovering a medical device carried by a guidewire from a vessel or other tubular conduit in a human body comprising:
  a tubular main body portion having distal and proximal ends and defining a first lumen sized to receive the medical device; and
  a guidewire receiving portion having distal and proximal ends and defining a second lumen sized for receiving the guidewire, the guidewire receiving portion being at least partially contained within the first lumen, the distal end of the guidewire receiving portion being movable with respect to the main body portion from a first position before recovery of the medical device into the first lumen to a second position after recovery of the medical device into the first lumen, the first position being distal of the second position.

9. The catheter according to claim 8, further comprising an exit port between the distal and proximal ends of the tubular main body.

10. The catheter according to claim 9, wherein during proximal retraction of the guidewire receiving portion, the proximal end of the guidewire receiving portion is retractable through the exit port.

11. The catheter according to claim 9, further comprising a stop to limit proximal retraction of the guidewire receiving portion.

12. The catheter according to claim 9, wherein the guidewire receiving portion communicates external to the catheter through the exit port.

13. The catheter according to claim 12, wherein the proximal end of the guidewire receiving portion is sealed to the catheter at the exit port.

14. The catheter according to claim 9, wherein at least a part of the guidewire receiving portion is corrugated.

15. The catheter according to claim 9, wherein at least a part of the guidewire receiving portion collapses during proximal retraction of the guidewire receiving portion.

16. The catheter according to claim 9, wherein the medical device is a filter basket.

17. The catheter according to claim 16, wherein when the guidewire receiving portion is in the second position, the filter basket is in the main body portion.

18. The recovery system according to claim 8, wherein the proximal end of the guidewire receiving portion extends through the exit port.

19. The catheter according to claim 8, wherein the guidewire receiving portion includes a line of perforation beginning at the distal end of the guidewire receiving portion.

20. A recovering system for recovering a medical device from a vessel or other tubular conduit in a human body comprising:
  a guidewire having a distal portion to which the medical device is connected;
  a catheter having a main body portion having distal and proximal ends and defining a first lumen sized to received the medical device; and
  a guidewire receiving portion having distal and proximal ends and defining a second lumen sized for receiving the guidewire, the guidewire receiving portion being at least partially contained within the first lumen, the distal end of the guidewire receiving portion being moveable with respect to the main body portion from a first position before recovery of the medical device into the first lumen to a second position proximal of the first position after recovery of the medical device into the first lumen, the distal end of the guidewire receiving portion being moved from the first position to the second position as the medical device is drawn proximally into the first lumen.

21. The recovering system according to claim 20, further comprising an exit port between the distal and proximal ends of the tubular main body.

22. The recovering system according to claim 21, wherein the proximal end of the guidewire receiving portion extends through the exit port.

23. The recovering system according to claim 20, further comprising a stop to limit proximal retraction of the guidewire receiving portion.

24. The recovering system according to claim 20, wherein a line of perforation is defined in the distal end of the guidewire receiving portion.

25. The recovering system according to claim 20, wherein the guidewire receiving portion communicates external to the catheter trough the exit port.

26. The recovering system according to claim 20, wherein the medical device is a filter basket.

* * * * *